United States Patent
Bos

(10) Patent No.: US 10,413,215 B2
(45) Date of Patent: Sep. 17, 2019

(54) MOBILE DEVICE AND METHOD FOR ANALYSING BREATH SAMPLES

(71) Applicant: eNose Holding B.V., Zutphen (NL)

(72) Inventor: Albert Bos, Brummen (NL)

(73) Assignee: eNose Holding B.V., Zutphen (NL)

( * ) Notice: Subject to any disclaimer, the term of this patent is extended or adjusted under 35 U.S.C. 154(b) by 328 days.

(21) Appl. No.: 14/391,558

(22) PCT Filed: Apr. 12, 2013

(86) PCT No.: PCT/NL2013/050266
§ 371 (c)(1),
(2) Date: Oct. 9, 2014

(87) PCT Pub. No.: WO2013/154431
PCT Pub. Date: Oct. 17, 2013

(65) Prior Publication Data
US 2015/0105683 A1 Apr. 16, 2015

(30) Foreign Application Priority Data
Apr. 12, 2012 (NL) ...................... 2008632

(51) Int. Cl.
*A61B 5/08* (2006.01)
*A61B 5/097* (2006.01)
(Continued)

(52) U.S. Cl.
CPC ............. *A61B 5/082* (2013.01); *A61B 5/097* (2013.01); *A61B 5/6898* (2013.01); *A61B 5/742* (2013.01);
(Continued)

(58) Field of Classification Search
CPC ......... A61B 5/082; A61B 5/097; A61B 5/742; A61B 5/7405; A61B 5/6898; G01N 27/12; G01N 33/497
See application file for complete search history.

(56) References Cited

U.S. PATENT DOCUMENTS 5,081,871 A * 1/1992 Glaser ................ A61B 5/083
422/84
6,046,054 A * 4/2000 McGeehin ............. G01N 27/12
422/90

(Continued)

FOREIGN PATENT DOCUMENTS

WO 03064994 A2 8/2003
WO 2007061294 A1 5/2007

OTHER PUBLICATIONS

Kort, Sharina, et al. "Data analysis of electronic nose technology in lung cancer: generating prediction models by means of Aethena." Journal of breath research 11.2 (2017): 026006.*

(Continued)

*Primary Examiner* — Christian Jang
*Assistant Examiner* — Andrey Shostak
(74) *Attorney, Agent, or Firm* — The Webb Law Firm

(57) ABSTRACT

Disclosed is a mobile device (15) for analyzing breath samples, comprising:—at least one mouthpiece (16) provided with at least one inlet opening (17) and at least one outlet opening (21) for allowing a person to respectively inhale and exhale via the mouthpiece,—at least one air filter (20) connected to the mouthpiece for filtering ambient air to be inhaled by the person,—at least one analysis compartment (19) connecting to the outlet opening of the mouthpiece and provided with at least one chemical trace detector (1), wherein the chemical trace detector comprises: at least one semi-conducting sensor (2); at least one heating element (4) for heating the semi-conducting sensor; at least one (Continued)

processor (6) for controlling the heating element; and a detection circuit (7) for detecting the change in resistance of the semi-conducting sensor which is at least partially determined by the presence of at least one chemical trace which reacts in the presence of the semi-conducting sensor.

15 Claims, 3 Drawing Sheets

(51) Int. Cl.
G01N 33/497 (2006.01)
G01N 27/12 (2006.01)
A61B 5/00 (2006.01)

(52) U.S. Cl.
CPC ........... *A61B 5/7405* (2013.01); *G01N 27/12* (2013.01); *G01N 33/497* (2013.01)

(56) References Cited

U.S. PATENT DOCUMENTS

| | | | | |
|---|---|---|---|---|
| 6,165,336 A | * | 12/2000 | Maki | G01N 27/4074 204/415 |
| 6,244,096 B1 | * | 6/2001 | Lewis | A61B 5/00 422/78 |
| 2003/0109794 A1 | * | 6/2003 | Phillips | A61B 5/097 600/543 |
| 2004/0204655 A1 | * | 10/2004 | Stock | A61B 5/097 600/532 |
| 2005/0214169 A1 | * | 9/2005 | Leddy | G01N 27/407 422/84 |
| 2006/0249160 A1 | * | 11/2006 | Scarberry | A61B 5/0836 128/207.13 |
| 2007/0062255 A1 | | 3/2007 | Talton | |
| 2007/0093725 A1 | * | 4/2007 | Shaw | A61B 5/097 600/543 |
| 2008/0078232 A1 | * | 4/2008 | Burke | G01N 33/497 73/23.3 |
| 2009/0215180 A1 | * | 8/2009 | Bos | G01N 27/122 436/8 |
| 2010/0121212 A1 | * | 5/2010 | Carlsson | A61B 5/097 600/538 |

OTHER PUBLICATIONS van de Goor, Rens, et al. "Training and Validating a Portable Electronic Nose for Lung Cancer Screening." Journal of Thoracic Oncology 13.5 (2018): 676-681.*

Chan, Daniel K., et al. "Breath testing for Barrett's esophagus using exhaled volatile organic compound profiling with an electronic nose device." Gastroenterology 152.1 (2017): 24-26.* van Geffen, Wouter H., Marcel Bruins, and Huib AM Kerstjens. "Diagnosing viral and bacterial respiratory infections in acute COPD exacerbations by an electronic nose: a pilot study." Journal of breath research 10.3 (2016): 036001.*

Kim et al.; "Microheater-Integrated Single Gas Sensor Array Chip Fabricated on Flexible Polyimide Substrate"; Sensors and Actuators: Chemical; Mar. 2006; pp. 410-417; vol. 114, No. 1; Elsevier, Switzerland.

Chen et al; "Chemical Sensors and Electronic Noses Based on 1-D Metal Oxide Nanostructures", IEEE Transactions on Nanotechnology; Nov. 2008; pp. 668-682; vol. 7, No. 6; New Jersey.

* cited by examiner

MOBILE DEVICE AND METHOD FOR ANALYSING BREATH SAMPLES

CROSS-REFERENCE TO RELATED APPLICATIONS

This application is the United States national phase of International Application No. PCT/NL2013/050266 filed Apr. 12, 2013, and claims priority to Netherlands Patent Application No. 2008632 filed Apr. 12, 2012, the disclosures of which are hereby incorporated in their entirety by reference.

BACKGROUND OF THE INVENTION

Field of the Invention

The invention relates to a mobile device for analysing breath samples. The invention also relates to a method for analysing breath samples, in particular by making use of a mobile device according to the invention. The invention also relates to a sensor for use in a mobile device according to the invention. The invention also relates to a mouthpiece for use in a device according to the invention.

Description of Related Art

The use of electronic noses makes it possible to determine a composition of gases in air exhaled by a person, from which one or more diseases of the person, such as for instance asthma, tuberculosis, diabetes, Parkinson, pneumonia and various types of cancer, can be diagnosed. Through comparison of breath profiles the electronic nose can be a diagnostic aid, providing that a disease or condition is sufficiently identifiable from a molecular pattern in the breath and thus, just as a fingerprint, leaves a unique breath-print. This breath-print is generally formed by the presence of one or more characteristic volatile organic compounds which are present as chemical traces in the breath and are produced during microbiological and biochemical processes in the body of a person. When a breath analysis is performed, breath samples are first taken from persons which are then analysed by analysis equipment elsewhere, generally at a central location. A known device for performing breath analyses is for instance described in the patent specification WO 03/064994. The use of breath analyses in the diagnosis of disease is advantageous from both a medical and economic viewpoint in that it is a non-invasive technique carried out at relatively low cost, partially with portable equipment and with the option of storing breath samples. A breath sample carried through the analysis apparatus can moreover be analysed relatively quickly. In addition to the above stated advantages, the known method also has several drawbacks. A drawback of the known device for performing breath analyses for the purpose of establishing clinical pictures is that from a logistical and practical viewpoint it is time-consuming and therefore deemed relatively inefficient. The reproducibility of the breath analyses is moreover found to be generally limited, which adversely affects the quality of the breath analysis. Due to their intrinsic complexity, the traditional electronic noses are less suitable for application in poorly conditioned environments (pressure and temperature fluctuations, dust, sand). In addition, the use of already developed analysis models with other electronic noses of the same type is problematic.

An object of the invention is to provide an improved device and method for performing breath analyses.

SUMMARY OF THE INVENTION

The invention provides for this purpose a mobile device for analysing breath samples having: at least one mouthpiece provided with at least one inlet opening and at least one outlet opening for allowing a person to respectively inhale and exhale via the mouthpiece, at least one air filter connected to the mouthpiece for filtering the air to be inhaled by the person, at least one analysis compartment connecting to the outlet opening of the mouthpiece and provided with at least one chemical trace detector, wherein the chemical trace detector comprises: at least one semi-conducting sensor; at least one heating element for heating the semi-conducting sensor; at least one processor for controlling the heating element; and a detection circuit for detecting the change in resistance of the semi-conducting sensor which is at least partially determined by the presence of at least one chemical trace which reacts in the presence of the semi-conducting sensor. The device according to the invention has several advantageous aspects. A first significant advantage of the device according to the invention is that a person blows the exhaled air directly along the at least one chemical trace detector, in particular the semi-conducting sensor thereof, whereby the exhaled air is analysed immediately and in situ, this significantly improving the efficiency from a logistical and technical viewpoint. Because the breath sample no longer need be stored but is analysed immediately, the risk of the breath sample degrading during storage is moreover precluded. Another significant advantage of the device according to the invention is that the inhaled air is purified before inhalation, whereby the composition of the inhaled air will be relatively well defined and substantially uniform, this enhancing the quality of the breath analysis. A further significant advantage is that use is made of a specific type of detector for analysing the exhaled air which can take a relatively compact form and using which breath samples can be analysed in relatively accurate and reproducible manner. Use is made here of the reactivity of characteristic chemical traces in the breath by subjecting these chemical traces at increased temperature to a redox reaction on or close to the semi-conducting sensor, this resulting in a detectable characteristic, usually temperature-dependent, change in resistance of the semi-conducting sensor. The reactive chemical traces are generally formed here by volatile organic compounds (voc) produced in the body. Using the chemical trace detector the presence of diverse reactive (oxidizable) chemical compounds in the breath can thus be determined, on the basis of which a clinical picture can be diagnosed. Non-oxidizable compounds such as carbon dioxide and inert gases will however not be detected here in direct manner by means of the chemical trace detector. In order to stimulate the occurrence of—a determined type of—redox reaction(s), a catalyst, usually manufactured from platinum or palladium, can optionally be arranged on the semi-conducting sensor. The semi-conducting sensor is preferably manufactured here from a semi-conductor, more preferably a metal oxide (MOS), in particular tin oxide, zinc oxide, iron oxide, tungsten oxide and/or cesium oxide. The material of the sensor is preferably manufactured from a sintered granular material, more preferably with semi-conductor properties. Applying a sintered granular material generally increases the effective sensor surface area, this enhancing the sensitivity of the sensor. At higher temperatures redox reactions take place with oxygen which is adsorbed to the sensor surface and which, depending on the temperature, can be present in different forms. In some cases it is also possible for a chemical trace, without the adsorbed oxygen, to itself undergo a redox reaction on the sensor surface, in particular the metal oxide surface. Both oxidation and reduction are therefore possible on the sensor surface. Measurable redox reactions take place substantially always on the surface (crystal lattice) and substantially not in the vicinity thereof. Chemical reactions with reactive particles, such as for instance desorbed radicals, could possibly take place above the sensor surface, although if no electrons are exchanged with a crystal lattice of the semi-conducting sensor it will generally not be possible to measure a change in resistance of the sensor. Chemical traces will thus usually first adsorb to the sensor surface, after which the chemical traces will react, followed by desorption of the reaction products. The detected temperature-dependent change in resistance is here the result of all chemical reactions taking place on the sensor surface at a determined temperature. The presence of one or more characteristic chemical traces or groups of chemical traces in the exhaled breath results in a (known) characteristic contribution toward the resistance change at a pre-known temperature. By measuring the resistance change at different temperatures a temperature-dependent pattern of resistance change is obtained which can be compared to one or more stored reference patterns, on the basis of which it is possible to determine relatively precisely which characteristic chemical traces are present in the breath.

The sensor as such can take a substantially plate-like form, which generally facilitates heating of the sensor by means of the heating element. The heating element is configured to heat the semi-conducting sensor to a typical temperature of between 200° C. and 600° C. It is important here to be able to precisely regulate the temperature of the heating element since the temperature usually determines the type of chemical compound (chemical trace) which reacts on the sensor surface, and is thereby related to a measured characteristic change in resistance of the sensor. The heating element will generally be of electrical nature and comprise one or more electrical resistor tracks. The processor is preferably configured here to regulate the specific resistance, and thereby the temperature, of the one or more resistor tracks. A further advantage of the applied chemical trace detector is that the detector is relatively insensitive to fluctuations in temperature and air humidity, this enhancing the applicability of the chemical trace detector. A suitable sensor is described in WO 2007/061294, the content of which forms part of this patent specification by way of reference. The device according to the invention further takes a mobile, preferably portable, form and is therefore relatively easy to displace and take to desired locations. It is in this way possible to take the device as such to the person to be examined, this being particularly practical and advantageous. The mobile character of the device according to the invention can provide substantial advantages, particularly in less developed countries.

In a preferred embodiment the processor of the chemical trace detector is configured to determine at least a part of the composition of the gas mixture exhaled by the person on the basis of the resistance change detected by the detection circuit. Comparing the detected resistance profile (resistance pattern) to a resistance profile, or information related thereto, prestored on a storage medium, generally in a database, makes it possible to determine on the basis of profile comparison and pattern recognition whether one or more characteristic chemical traces do or do not occur in the air exhaled by the person. During detection of the presence of a characteristic chemical compound or group of compounds in the exhaled air an auditive and/or visual signal can be generated by a signal-generating element coupled to the processor. It is also possible to envisage a signal being generated by the signal-generating element after each measurement, but wherein the nature of the signal depends on the analysis results. The signal has the purpose of alerting the person and/or a healthcare professional to the presence or absence of one or more characteristic traces in the breath of the person in question.

In a preferred embodiment the at least one inlet opening is provided with a displaceable closing valve configured to open the inlet opening when the person inhales and to close the inlet opening when the person exhales. By having the closing valve function as a one-way valve (non-return valve) ambient air can be drawn in relatively unimpeded and the exhaled air is prevented from leaving the device via the inlet opening, whereby the exhaled air is pushed through the outlet opening into the analysis compartment. The at least one outlet opening of the mouthpiece is preferably provided with a displaceable closing valve configured to close the inlet opening when the person inhales and to open the inlet opening when the person exhales. This closing valve functions as non-return valve which allows only exhaled air to be blown into the analysis compartment, and prevents a reverse airflow. It is possible to envisage applying only one shared closing valve in the mouthpiece which closes and opens the inlet opening and simultaneously opens and closes the outlet opening in selective manner subject to inhalation or exhalation taking place.

In order to filter the air drawn in by the person via the mouthpiece before it is inhaled, a carbon filter can be applied as filter element. The carbon filter generally absorbs a substantial part of the volatile organic compounds present in the ambient air, whereby they will not be inhaled by the person and cannot therefore influence the final breath analysis either, which will generally enhance the quality of the breath test.

When the person exhales into the mouthpiece, the person will usually also exhale liquid, particularly water vapour and/or saliva. In order to prevent moistening and in particular contamination of the analysis compartment, it is advantageous for the device to comprise at least one liquid filter and/or bacteria filter positioned in or close to the at least one outlet opening. It is possible here to envisage the liquid filter and the bacteria filter being formed by the same filter. An example of such a filter is a High Efficiency Particulate Air (HEPA) filter. It is however important for the applied filter to be sufficiently porous (open) to enable relatively easy blowing of the exhaled air through the filter during exhaling without the person being considerably inconvenienced. When such a filter is applied, liquids and/or bacteria exhaled by the person will remain in the at least one outlet filter of the mouthpiece. After use of the device the at least one outlet filter and/or the mouthpiece as a whole can be replaced by an unused or a cleaned one. It is possible to envisage only a part of the mouthpiece having to be replaced if the system is only used by one and the same person for the purpose of monitoring a determined clinical picture.

It can further be particularly advantageous for the device to comprise at least one selective gas filter, in particular a selective membrane, positioned in or close to the at least one outlet opening. The gas filter is configured here to selectively allow or prevent passage of specific compounds. The gas filter will here generally allow passage of characteristic chemical traces, which are defining for the diagnosis of a clinical picture, to the analysis compartment, while other gaseous compounds, such as one or more inert gases and/or one or more gases which could disrupt the analysis, can be removed. The selective gas filter will generally also be configured as liquid filter and may optionally also be configured as bacterial filter.

The analysis compartment can be formed by a (flexible) bag into which the exhaled air can be blown via the mouthpiece, and wherein the chemical trace detector is at least partially received in the bag. It is however generally more advantageous from a structural and hygienic viewpoint to apply a substantially form-retaining analysis compartment, wherein the analysis compartment preferably takes a substantially channel-like form. This makes it possible to bring the exhaled air into relatively good and intensive contact with the chemical trace detector, this generally enhancing the quality of the breath analysis. In order to enable removal of air blown into the analysis compartment it is advantageous for the analysis compartment to be provided with at least one outlet opening for discharging at least a part of the air exhaled into the device, whereby it is in fact possible to blow through the analysis compartment. The chemical trace detector will usually be positioned between an inlet opening of the analysis compartment connecting to the outlet opening of the mouthpiece and the outlet opening of the analysis compartment, whereby the exhaled air is blown along the at least one chemical trace detector. It is advantageous here for the at least one outlet opening of the analysis compartment to be provided with at least one closing valve configured to open the outlet opening when the person exhales into the analysis compartment via the mouthpiece. When the person inhales via the mouthpiece, the closing valve of the analysis compartment will remain closed, whereby air can only be drawn in via the at least one inlet opening of the mouthpiece. In a preferred embodiment the device comprises at least one preconcentrator for temporarily binding by means of adsorption one or more gas components exhaled by a person. The preconcentrator will generally be arranged here in the analysis compartment. Once the person has blown into the analysis compartment for a sufficient length of time, the gas components present on or in the preconcentrator are released therefrom by means of heating and, preferably via a pump system, guided along the at least one chemical trace detector. The preconcentrator can be cleaned after use by removing components which may still be bound thereto. Use is preferably made here of the circulating system which draws in and guides optionally purified ambient air through or along the preconcentrator. The preconcentrator can optionally be heated here to enable improved cleaning.

It is advantageous for the mouthpiece to be releasably connected to the analysis compartment. The relatively inexpensive mouthpiece will usually be contaminated most during use of the device. Releasable coupling of the mouthpiece to the analysis compartment enables relatively simple removal of the mouthpiece from the analysis compartment, after which the mouthpiece can be cleaned or replaced by another. In order to achieve a substantially medium-tight connection between the mouthpiece and the analysis compartment it is advantageous for the mouthpiece and the analysis compartment to be mutually connected via a sealing element. The sealing element will generally be manufactured here from a polymer, in particular an elastomer such as rubber. The sealing element will generally take an annular form to enable realization of a relatively reliable peripheral seal.

The mouthpiece can be configured to be partially received in the oral cavity of a person. The mouthpiece can be provided for this purpose with a spout-like outer end which can be received at least partially in the mouth of a person. The person can then inhale and exhale via this spout-like outer end, whereby the person can blow the breath relatively forcefully into the mouthpiece and the analysis compartment. It is also possible to envisage the mouthpiece being configured to enclose the mouth and at least a part of the nose of a person, whereby the person can breathe through both the mouth and the nose via the mouthpiece. The mouthpiece can even be embodied here as a face mask which can optionally be connected to the head of the person.

In order to prevent gas and liquid exchange with the surrounding area, which could have an adverse effect on the breath test, the mouthpiece and a housing of the analysis compartment are manufactured from a substantially impermeable (gas-tight) material. The mouthpiece and the housing of the analysis compartment will generally be manufactured at least partially from an impermeable polymer such as ABS or PVC.

In order to ensure as far as possible the mobile character of the device according to the invention, it is advantageous for the device to comprise at least one electrical energy source coupled to the at least one chemical trace detector. Incorporating an energy source in the device to allow operation of particularly the chemical trace detector enables fully autonomous functioning of the device. The energy source will generally be formed here by a battery, fuel cell or accumulator. In an alternative embodiment it is also possible to envisage having at least a part of the energy source being formed by at least one solar panel, which can be particularly advantageous, especially in less developed countries.

The device can take a portable form and can be held during use by the person to be tested. It is advantageous here for the device to comprise at least one handle. In an alternative embodiment the device may comprise a carrier frame, such as a stand, to allow the device to support on the fixed world. The device optionally comprises one or more support wheels in order to make the device mobile. It is possible here to envisage the device being mounted on a vehicle.

The invention also relates to a method for analysing breath samples, for example by making use of the mobile device according to the invention, comprising of: A) having a person inhale purified air via a mouthpiece, B) having the person exhale air into an analysis compartment via the mouthpiece, and C) analysing at least a part of the composition of the exhaled air using at least one chemical trace detector in the analysis compartment by detecting the change in resistance of a heated semi-conducting sensor of the chemical trace detector corresponding to the presence of at least one chemical trace which reacts in the presence of the semi-conducting sensor. The increased temperature of the semi-conducting sensor results in chemical reaction of one or more (oxidizable) chemical traces, whereby a detectable characteristic change in resistance occurs. The presence of one or more chemical traces characteristic of a clinical picture can in this way be determined. An auditive and/or visual signal can be generated during step D) of the method according to the invention when one or more characteristic chemical traces are determined. Further embodiment variants of the method according to the invention have already been described at length in the foregoing.

The invention further relates to a chemical trace detector for use in a device according to the invention. The invention further relates to a mouthpiece for use in a device according to the invention.

BRIEF DESCRIPTION OF THE DRAWINGS

The invention will be elucidated with reference to non-limitative exemplary embodiments shown in the following figures. Herein.

DETAILED DESCRIPTION OF THE INVENTION

Figure 1:
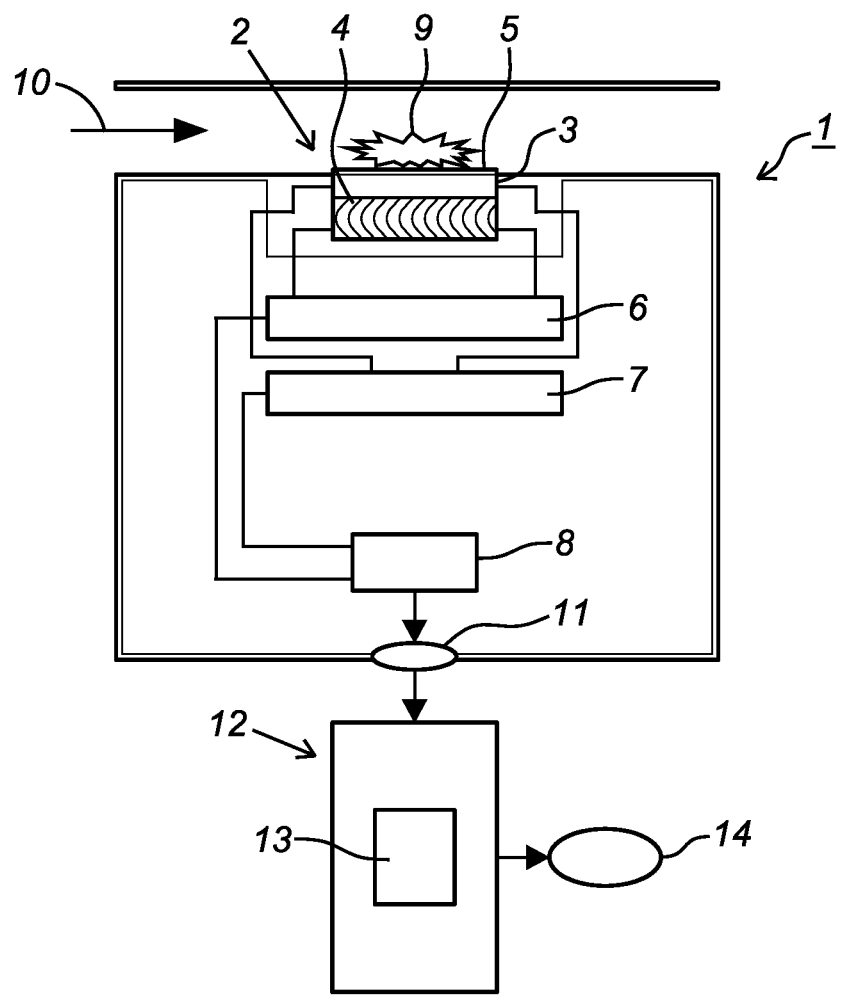
FIG. 1 is a schematic view of a chemical trace detector for use in a device according to the invention.

FIG. 1 is a schematic view of a chemical trace detector 1 for use in a device according to the invention. Detector 1 comprises here a heatable semi-conducting sensor 2 which is also referred to as hotplate sensor. Semi-conducting sensor 2 preferably comprises a metal oxide layer 3 which is sensitive to chemical reactions taking place in the immediate vicinity, and a heating element 4 for heating the metal oxide layer 3. The metal oxide layer 3 exhibits a change in resistance subject to chemical traces which react on or close to a free surface 5 of the metal oxide layer 3. Heating element 4 is preferably mounted on or close to the metal oxide layer 3 and is preferably manufactured by means of Micro-Electrical Mechanical Systems (MEMS) technology, so that the temperature of metal oxide layer 3 will be substantially identical to the temperature of heating element 4. Heating element 4 has a low thermal mass and is controlled by a processor 6 for the purpose of realizing a stable temperature in the metal oxide layer 3. This is usually achieved by applying a separate electronic circuit provided with one or more Wheatstone bridges. The metal oxide layer 3 is coupled to a detection circuit 7 for detecting the resistance change resulting from the presence of a chemical trace which reacts on or close to the (heated) semi-conducting sensor 2. The values measured by detection circuit 7 are stored on an internal memory 8, such as a flash memory or other type of memory. One or more detected resistance values are stored in internal memory 8 as cross-reference to one or more predefined temperatures, so that a footprint is generated of one or more chemical compounds 9 which form part of an exhaled airflow 10. The information stored in memory 8 is compared via a communication connection 11 to a database 13 stored on a storage medium 12 and provided with predefined footprints for known characteristic chemical compounds. Storage medium 12 and the associated database 13 are wholly incorporated in the device according to the invention, wherein communication connection 11 takes place in fully wired manner. In an alternative preferred embodiment storage medium 12 is present at a different location and communication connection 11 preferably takes place wirelessly. By comparing the detected footprint to the footprint(s) stored in database 13 it is possible to determine whether there is a best match 14, and the presence of one or more characteristic chemical compounds in the exhaled air can be determined. The comparison and identification of footprints takes place here by means of known pattern recognition and identification software.

Figure 2:
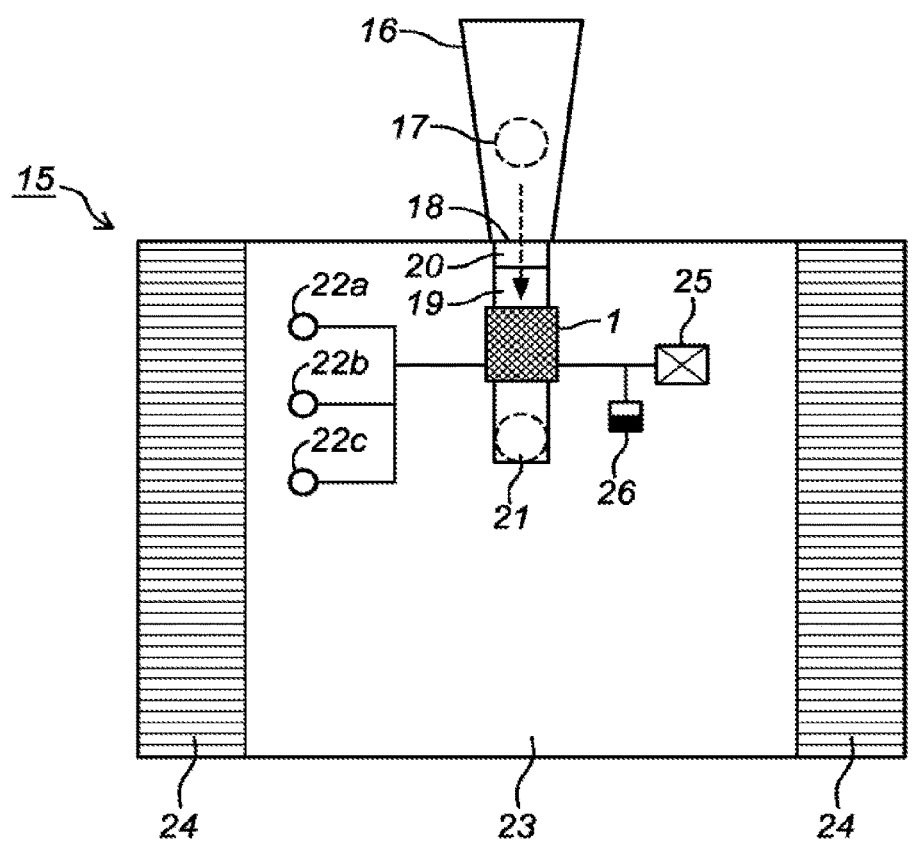
FIG. 2 is a cut-away front view of a device according to the invention in which the chemical trace detector according to FIG. 1 is incorporated.
Figure 3:
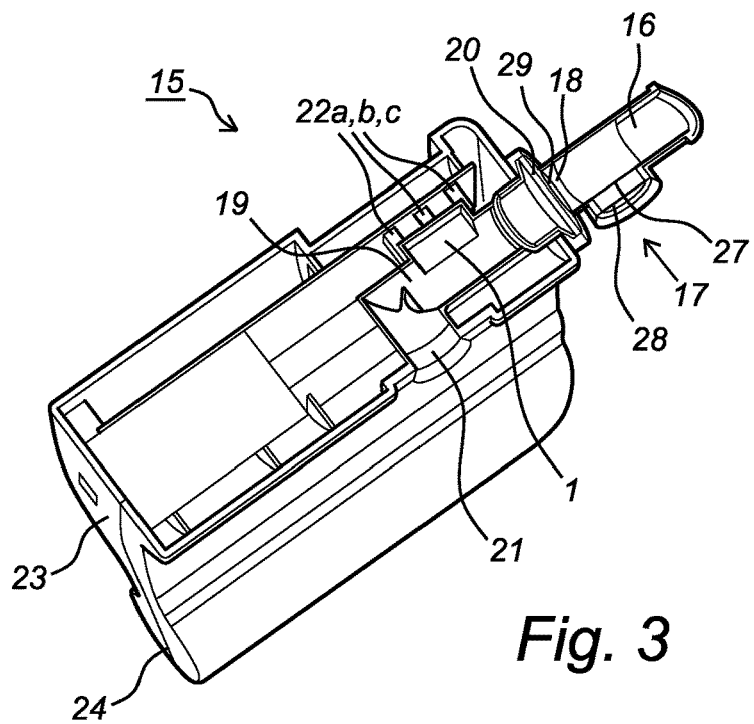
FIG. 3 shows a cross-section of the device according to FIG. 2.
Figure 4:
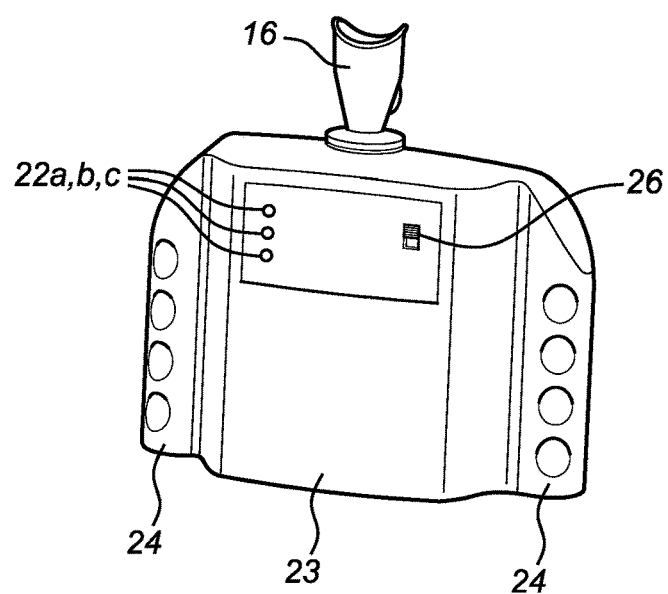
FIG. 4 is a perspective view of the device according to FIGS. 2 and 3.

FIG. 2 is a cut-away schematic front view of a portable device 15 according to the invention incorporating the chemical trace detector 1 according to FIG. 1. Device 15 comprises a mouthpiece 16 provided with a closable inlet opening 17 and a closable outlet opening 18. Positioned close to or in inlet opening 17 is an air filter (not shown) for filtering air drawn in via the inlet opening. Mouthpiece 16 is configured for co-action with the mouth of a person. The person can inhale via mouthpiece 16, wherein air is drawn in and filtered via inlet opening 17, and exhale, wherein air is blown via outlet opening 18 out of mouthpiece 16 into an analysis compartment 19. Outlet opening 18 is closed during inhalation and inlet opening 17 is closed during exhalation. A bacterial filter 20, in particular a HEPA filter, is arranged between outlet opening 18 and analysis compartment 19 for filtering bacteria and saliva residues out of the exhaled air. This bacterial filter will usually form part of mouthpiece 16. Analysis compartment 19 takes a channel-like form and is provided at an outer end remote from mouthpiece 16 with a closable outlet opening 21 in order to enable a person to blow through analysis compartment 19. The chemical trace detector 1 is arranged in analysis compartment 19 for analysing passing exhaled air. The chemical trace detector 1 is coupled to preferably three different coloured LEDs (red, orange, green) 22a, 22b, 22c for generating a visual signal subject to the outcome of the footprint comparison. LEDs 22a, 22b, 22c are arranged here in an (outer) housing 23. Housing 23 is provided here with two profiled handles 24 allowing device 15 to be held fixedly. Device 1 further comprises a battery 25 for the purpose of providing detector 1 with electrical energy, and a switch 26 for switching device 1 on and off FIG. 3 shows a cross-section of device 15 according to FIG. 2. This figure shows particularly that inlet opening 17 is provided with a selective closing valve 27, wherein an air filter 28, in particular a carbon filter, is arranged upstream relative to inlet opening 17 for filtering the air before it is drawn via inlet opening 17 into mouthpiece 16 by an inhaling person. Further shown is that bacterial filter 20 is positioned downstream relative to outlet opening 18 of the mouthpiece, wherein outlet opening 18 is also provided with a closing valve 29. The resistance of bacterial filter 20 preferably has to be such that bacteria and saliva residues are filtered out by filter 20 while a person can blow exhaled air relatively easily through filter 20. Outlet opening 21 of analysis compartment 19 on the one hand and LEDs 22a, 22b, 22c on the other are situated on opposite sides of housing 23 so that a person looking at the selective illumination of LEDs 22a, 22b, 22c is not exposed to exhaled air, which generally leaves outlet opening 21 of analysis compartment 19 at relatively high speed. FIG. 4 also shows a perspective view of the device according to FIGS. 2 and 3.

It will be apparent that the invention is not limited to the exemplary embodiments shown and described here, but that within the scope of the appended claims numerous variants are possible which will be self-evident to the skilled person in the field.

The invention claimed is:

1. A portable and autonomous device for analysing breath samples for the diagnosis of diseases or physical conditions, comprising:

at least one mouthpiece provided with at least one inlet opening and at least one outlet opening for allowing a person to respectively inhale and exhale via the mouthpiece, wherein the at least one inlet opening is provided with a displaceable closing valve configured to open the inlet opening when the person inhales and to close the inlet opening when the person exhales so that only inhaled air passes through the at least one inlet opening, and wherein the at least one outlet opening of the mouthpiece is provided with a displaceable closing valve configured to close the outlet opening of the mouthpiece when the person inhales and to open the outlet opening of the mouthpiece when the person exhales so that only exhaled air passes through the at least one outlet opening of the mouthpiece, at least one air filter connected to the mouthpiece for filtering ambient air to be inhaled by the person through the at least one inlet opening, at least one exhaled air filter positioned in or close to the at least one outlet opening of the mouthpiece, wherein the at least one exhaled air filter is configured as a selective gas filter allowing passage of characteristic chemical traces, and wherein the at least one exhaled air filter is further configured as a bacterial filter for filtering bacteria and saliva residues out of the exhaled air that is exhaled through the at least one outlet opening of the mouthpiece, and at least one analysis compartment connecting to the outlet opening of the mouthpiece, wherein the displaceable closing valve provided with the at least one outlet opening of the mouthpiece is configured to permit only the exhaled air to pass into the analysis compartment, wherein the at least one analysis compartment is provided with at least one chemical trace detector, wherein the chemical trace detector comprises:

a plurality of semi-conducting sensors;

a plurality of heating elements for heating the semi-conducting sensors;

at least one processor for controlling the heating elements to heat each semi-conducting sensor to a predefined temperature, respectively; and a detection circuit for detecting the change in resistance of each semi-conducting sensor at said predefined temperature, wherein the change in resistance is at least partially determined by the presence of at least one chemical trace which reacts in the presence of the plurality of semi-conducting sensors to create a temperature-dependent pattern of resistance changes which can be compared to one or more stored reference patterns to determine the presence of the characteristic chemical traces in the exhaled air, wherein the analysis compartment is provided with at least one outlet opening for discharging from the analysis compartment at least a part of the exhaled air, wherein the at least one outlet opening of the analysis compartment is provided with at least one closing valve configured to open the at least one outlet opening of the analysis compartment when the person exhales into the analysis compartment via the mouthpiece, and wherein the device is configured such that the exhaled air is blown directly along the at least one chemical trace detector.

2. The device as claimed in claim 1, wherein the processor of the chemical trace detector is configured to determine at least a part of the composition of the exhaled air by the person on the basis of the change in resistance detected by the detection circuit.

3. The device as claimed in claim 2, wherein the device comprises at least one storage medium on which information related to at least one chemical trace is stored, and wherein the processor is configured to compare the determined composition of at least a part of the exhaled air to the information stored on the storage medium.

4. The device as claimed in claim 1, wherein the device comprises at least one signal-generating element coupled to the processor for generating an auditive and/or visual signal following detection in the exhaled air of the presence of a chemical trace about which information is stored on a storage medium.

5. The device as claimed in claim 1, wherein the at least one exhaled air filter is formed by a carbon filter.

6. The device as claimed in claim 1, wherein the device comprises at least one preconcentrator for temporarily binding at least one chemical compound exhaled by the person.

7. The device as claimed in claim 1, wherein the mouthpiece is releasably connected to the analysis compartment.

8. The device as claimed in claim 1, wherein the mouthpiece and the analysis compartment are mutually connected via a sealing element.

9. The device as claimed in claim 1, wherein the mouthpiece is configured to be received at least partially in the mouth of the person.

10. The device as claimed in claim 9, wherein the mouthpiece is configured as a face mask.

11. The device as claimed in claim 1, wherein the mouthpiece and a housing of the analysis compartment are manufactured from a substantially impermeable material.

12. The device as claimed in claim 1, wherein the device comprises at least one handle for the purpose of carrying the device.

13. A method for analysing breath samples for the diagnosis of diseases or physical conditions by using the portable and autonomous device according to claim 1, comprising the steps of:

having a person inhale purified air via the mouthpiece of the device according to claim 1, having the person exhale air into the at least one analysis compartment of the device according to claim 1 via the mouthpiece, wherein the exhaled air is blown directly along the at least one chemical trace detector in the analysis compartment, and analysing at least a part of the composition of the exhaled air using the at least one chemical trace detector in the analysis compartment by detecting the change in resistance of a heated semi-conducting sensor of the chemical trace detector corresponding to the presence of at least one chemical trace which reacts in the presence of the plurality of semi-conducting sensors.

14. The method as claimed in claim 13, wherein the presence of at least one symptomatic chemical trace in the exhaled air is determined during the analysing step using the chemical trace detector.

15. The method as claimed in claim 14, wherein the method further comprises generating an auditive and/or visual signal once the presence has been established of at least one symptomatic chemical trace.

* * * * *